United States Patent
Poston et al.

(10) Patent No.: US 9,687,027 B2
(45) Date of Patent: Jun. 27, 2017

(54) DEVICE FOR VAPORIZING LIQUID FOR INHALATION

(71) Applicant: GHT GLOBAL HEATING TECHNOLOGIES AG, Baar, OT (CH)

(72) Inventors: Jeffrey Poston, Florence, KY (US); Lawrence Weber, Holbrook, NY (US); Giampaolo Vacca, Loveland, OH (US); Pavlo Bagriy, Maineville, OH (US)

(73) Assignee: GHT GLOBAL HEATING TECHNOLOGIES AG, Baar (CH)

( * ) Notice: Subject to any disclaimer, the term of this patent is extended or adjusted under 35 U.S.C. 154(b) by 394 days.

(21) Appl. No.: 14/022,744

(22) Filed: Sep. 10, 2013

(65) Prior Publication Data

US 2014/0069424 A1    Mar. 13, 2014

Related U.S. Application Data

(60) Provisional application No. 61/699,101, filed on Sep. 10, 2012.

(51) Int. Cl.
| | | |
|---|---|---|
| H05B 3/00 | (2006.01) |
| A24F 47/00 | (2006.01) |
| A61M 15/06 | (2006.01) |
| A61M 15/00 | (2006.01) |
| A61M 11/04 | (2006.01) |

(Continued)

(52) U.S. Cl.
CPC ......... *A24F 47/008* (2013.01); *A61M 11/042* (2014.02); *A61M 11/047* (2014.02); *A61M 15/0085* (2013.01); *A61M 15/06* (2013.01); *A61M 11/007* (2014.02); *A61M 2016/0021* (2013.01); *A61M 2016/0039* (2013.01); *A61M 2205/3653* (2013.01); *A61M 2205/8206* (2013.01)

(58) Field of Classification Search
CPC . A61K 31/465; A61M 15/06; A61M 15/0091; A61M 11/042; A61M 11/02; A61M 11/041; A61M 2210/0625; A61M 15/0028; A24F 47/008; A24F 47/002; A24F 7/02; B05B 11/0054; B05B 11/02; B05B 11/3091
See application file for complete search history.

(56) References Cited

U.S. PATENT DOCUMENTS

| | | | | |
|---|---|---|---|---|
| 3,636,949 A | * | 1/1972 | Kropp ............... | A61M 15/0026 128/200.23 |
| 5,651,397 A | * | 7/1997 | Black ................... | A61C 5/064 141/18 |
| 8,915,254 B2 | * | 12/2014 | Monsees .............. | A24F 47/006 131/194 |

FOREIGN PATENT DOCUMENTS

IE    WO 2011125058 A1 * 10/2011    .......... A61M 11/047

* cited by examiner

*Primary Examiner* — Bradley Philips
*Assistant Examiner* — Victoria Leszczak
(74) *Attorney, Agent, or Firm* — Jenei LLC

(57) ABSTRACT

A device atomizes or vaporizes a liquid for inhalation. A housing has a proximal exit orifice that communicates with an intake orifice. A housing encompasses a reservoir containing a liquid. A wick has a first end in contact with the liquid and a second end that is exposed at an opening in the reservoir. A heater is disposed within housing in an air passage that communicates between the intake orifice and the proximal exit orifice. An actuator responds to a user of the device by placing the heater and the second end of the wick into proximity with the heater to vaporize the liquid.

21 Claims, 6 Drawing Sheets

(51) Int. Cl.
*A61M 16/00* (2006.01)
*A61M 11/00* (2006.01)

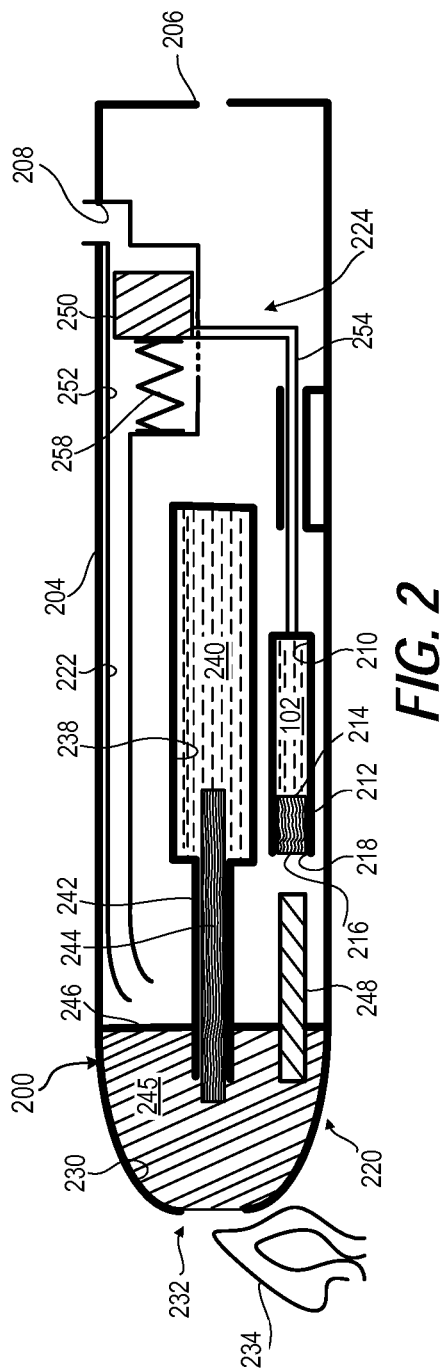
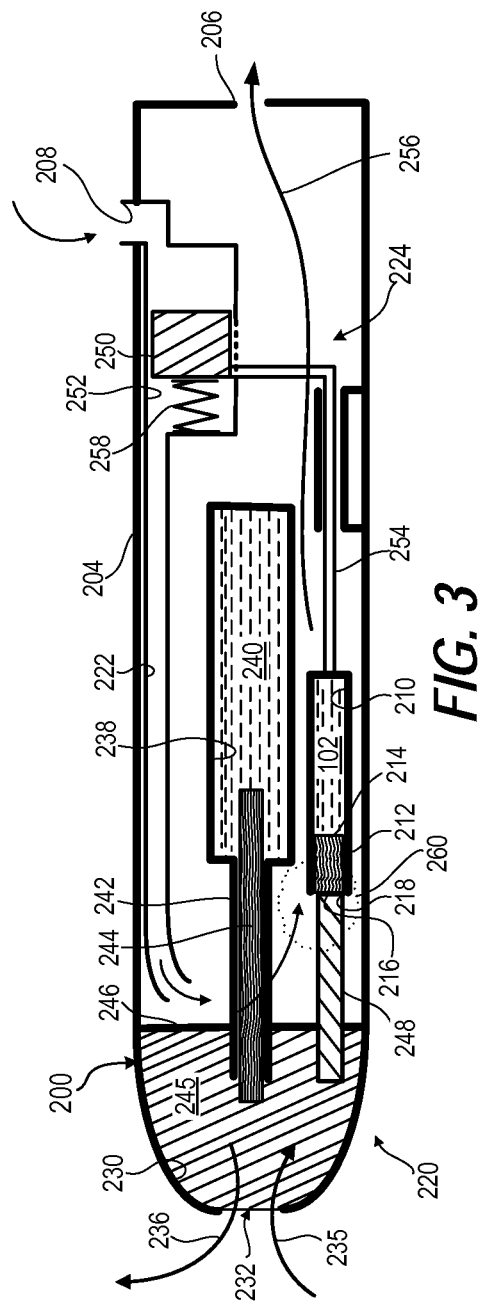

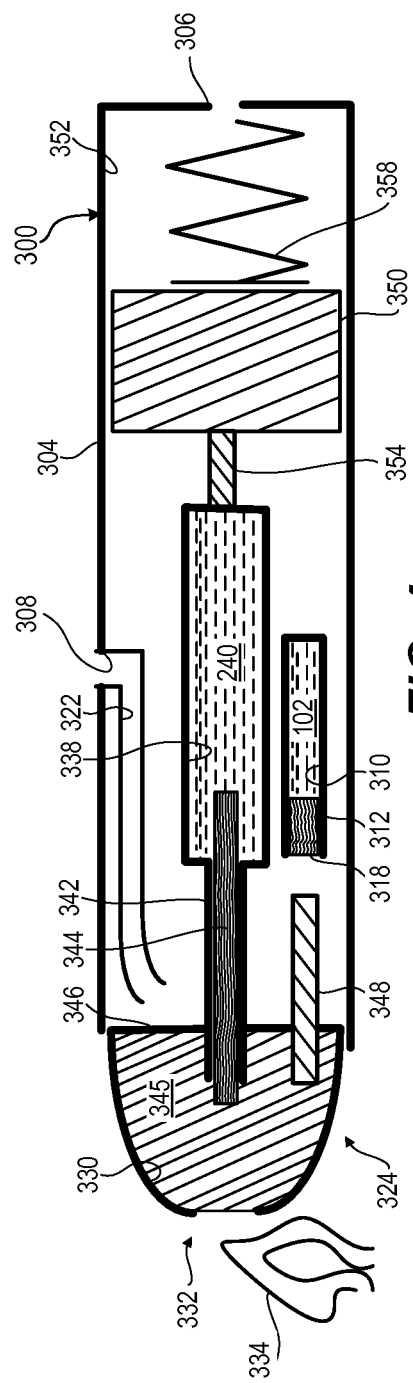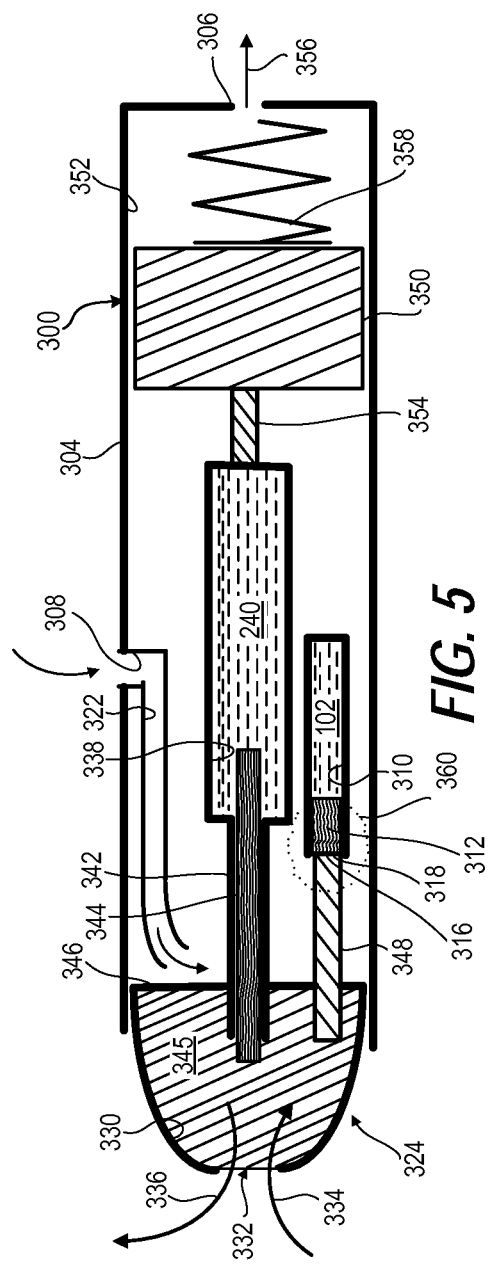
FIG. 4
FIG. 5

DEVICE FOR VAPORIZING LIQUID FOR INHALATION

CROSS-REFERENCE TO RELATED APPLICATIONS

The present application is a continuation-in-part to and claims priority to provisional U.S. Patent Application No. 61/699,101, filed Sep. 10, 2012, which application is herein incorporated by reference in its entirety for all purposes.

BACKGROUND OF THE INVENTION

1. Field of the Invention

The field of art disclosed herein pertains to devices that vaporize a liquid for inhalation.

2. Description of the Related Art

The current state of the art in smokeless tobacco/nicotine is the e cigarette. The e cigarette is a device that heats a liquid to vaporize it. This vapor is inhaled as the smoke from a traditional cigarette would be. The heating is done via an electric heater (typically a nichrome wire), which is turned on by either a pushbutton on the e-cigarette or by a pressure switch, which starts the heating when the user "draws" on the e-cigarette.

SUMMARY OF THE INVENTION

In one aspect, the present disclosure provides a device that atomizes or vaporizes a liquid for inhalation. A housing has a proximal exit orifice that communicates with an intake orifice. A housing encompasses a reservoir containing a liquid. A wick has a first end in contact with the liquid and a second end that is exposed at an opening in the reservoir. A heater is disposed within housing in an air passage that communicates between the intake orifice and the proximal exit orifice. An actuator responds to a user of the device by placing the heater and the second end of the wick into proximity with the heater to vaporize the liquid.

These and other features are explained more fully in the embodiments illustrated below. It should be understood that in general the features of one embodiment also may be used in combination with features of another embodiment and that the embodiments are not intended to limit the scope of the invention.

BRIEF DESCRIPTION OF THE DRAWINGS

The various exemplary embodiments of the present invention, which will become more apparent as the description proceeds, are described in the following detailed description in conjunction with the accompanying drawings, in which:

FIG. 2 depicts a diagram of a device for vaporizing a liquid for inhalation using a catalytic heater and pneumatic actuator depicted in an unactuated state according to one embodiment.

FIG. 3 depicts a diagram of the device of FIG. 2 in an actuated state.

FIG. 4 depicts a diagram of a device for vaporizing a liquid for inhalation using a catalytic heater an alternative pneumatic actuator, depicted in an unactuated state, according to one embodiment.

FIG. 5 depicts a diagram of the device of FIG. 4 in an actuated state.

DETAILED DESCRIPTION

Figure 1:
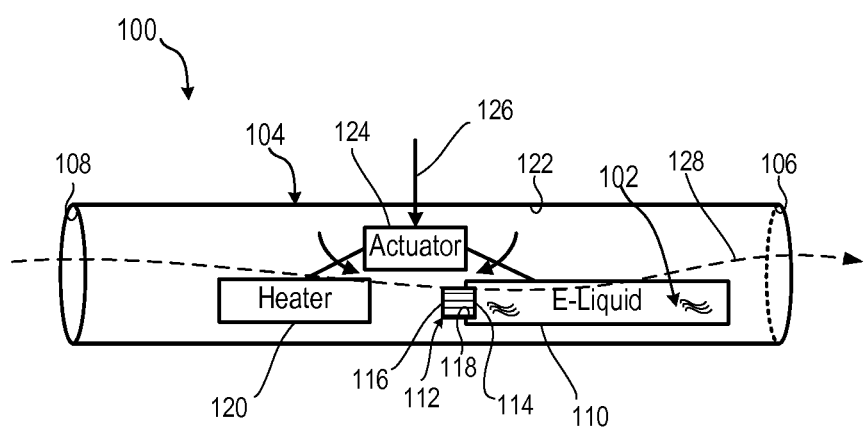
FIG. 1 depicts a diagram of a device for vaporizing a liquid for inhalation by using a heater according to one embodiment.

The present innovation relates generally to a device for atomizing or vaporizing a liquid for inhalation by selectively heating the liquid in a device from which a user draws a breath. In a particular aspect, the device may utilize a catalytic heater rather than an electric heater. The flameless catalytic heater may be lit in a fashion similar to that of a traditional cigarette. Once the lighter or match is removed the catalyst will then flamelessly combust the fuel. The air used for fuel combustion as well as the exhaust air from the combustion is preferably kept separate from the air drawn by the user. Additionally, the catalytic heater is slower to respond than the electric so starting and stopping the catalytic heater is not practical during a specific session of use. For this reason it is more practical to keep the heater going and bring the e-liquid into intermittent thermal contact with the heat source.

In one embodiment the catalytic heater would be at the tip of the artificial cigarette just as the lit end of a traditional cigarette. At or near the back side of the heater is a sealed wall to isolate the combustion air and the combustion exhaust away from the air to be drawn in by the consumer. Thru this sealed wall passes a tube to carry fuel from the fuel reservoir located closer to the middle of the artificial cigarette. The tube may contain one or more wicks and other fuel rate regulating mechanisms in order to facilitate the transfer of fuel from the fuel reservoir to the catalyst regardless of orientation and at a consistent rate. Either the hot back of the sealed wall can be used to vaporize the drug or chemical containing liquid or a thermal conductor may be placed on or through the sealed wall.

The thermal conductor may extend into the catalytic heater to increase the thermal transfer into the thermal conductor and the thermal conductor may extend into the air cavity to facilitate the heat transfer into the e-liquid. If the thermal conductor goes through the sealed wall it will need to be sealed to avoid exhaust being drawn in. This seal can be via a device like a grommet which could be of a rubber type (or other material which could both insulate thermally and seal) material which would seal as well as insulate the thermal conductor from the sealed wall or it could be something thermally conductive to allow for the transfer of heat between the sealed wall and the thermal conductor.

A reservoir containing e-liquid may be in the middle region of the artificial cigarette. Either the entire reservoir or just the wick is kept at a distance from the thermal conductor (or the sealed wall if no further thermal conductor is needed) by a spring, either directly or indirectly. The spring pressure can be overcome to force the contact of the e-liquid wick with the thermal conductor. This may be accomplished through the use of a plunger activated by the vacuum produced by the consumer drawing on the artificial cigarette. Alternatively, proximity or contact between the wick and a heater or heated surface may be accomplished by a simple button or lever pressed by the consumer's finger or lips which initiates the vaporization. The intake of air may be very close to the consumer to keep it far from the combustion products. A pipe or tube of some sort can then bring this fresh air near to the vaporization area thereby encouraging the vapor to escape through the draw. Additionally the plunger can be incorporated into this path if the desire is to push some component away from the consumer to contact the heated area. For example the e-liquid reservoir or its wick toward the thermal conductor.

In certain implementations, the e-liquid reservoir and the fuel reservoir may be removable and insertable. For example, the e-liquid reservoir and the fuel reservoir may be contained in one disposable unit. In this way the consumer can gain additional fuel and e-liquid in one action while the catalytic heater and other components can remain in a reusable device. In some designs it may be desirable to have the fuel and e-liquid reservoir(s) refillable, either within the artificial cigarette, especially if not removable, or after removing them if so enabled.

For the purposes of this disclosure the term "e-liquid" refers to any liquid to be atomized or vaporized for inhalation. This includes, but is not limited to tobacco and related items such as nicotine, marijuana and related items, medications to be vaporized as well as other inhalables.

In another embodiment the plunger could also be set in the opposite direction by placing it in the airflow as it returns toward the consumer if the desire is to pull some component closer to the consumer. For example the thermal conductor could move toward the e-liquid, or the entire heater could move toward the smoke juice.

Additionally another embodiment could have a button, which is pressed by the consumer to initiate the vaporization. And in yet another embodiment a lever could be on the mouthpiece, which the user moves with a biting action to initiate the vaporization.

In another embodiment the heater could be closer to the center of the artificial cigarette with fuel and or e-liquid farther away from the consumer. This configuration could make the e-liquid and or fuel more convenient to replace.

Additionally the design can be such that the air is heated so that the user has the added sensation of breathing in warmer air to better simulate a cigarette. As one example the intake pipe which brings the air from near the consumer to near the thermal conductor could itself be in thermal contact with the thermal conductor, or the sealed wall if it conducts sufficient amounts of heat, so that the incoming air is drawn through a warm pipe before reaching the vapor. This could both assist in maintaining a vapor with less potential to condense out before arriving at the consumer as well as provide the heating sensation.

Additionally the fuel and or e-liquid reservoir could be on the heater side of the sealed wall.

Additionally a small battery could be used to power non-atomization features, including, but not limited to, electric heater start of catalysis, temperature management, visual effects such as lights, etc.

For example, a device may be comprised of a heater; a reservoir of liquid to be atomized; a mouthpiece on which a person can draw a partial vacuum; a spring which holds the wick away from the heat and; a plunger which can convert the partial vacuum to overcome the spring pressure; thus causing the intermittent atomization of a liquid by means of moving a heated object into contact with a wick, in fluid contact with a liquid, utilizing a partial vacuum produced by the operator drawing "sucking" on one end of the device which overcomes a spring pressure in the other direction.

For example, such a device may incorporate actuating by moving the wick toward the heater.

For another example, such a device may incorporate a wick that remains in thermal contact with the heater and is intermittently in fluid contact with the liquid.

For an additional example, such a device may add heat to the air drawn in by a user to add to the feel of the simulated cigarette to make it more like a normal cigarette. For instance, the heated air may be utilized to atomize the e-liquid from the wick.

In one embodiment, the invention provides for an aerosol generating system. In one embodiment, the aerosol generating system is a smoking system.

In one embodiment, the aerosol-forming substrate is a liquid aerosol-forming substrate.

In another embodiment, the heated aerosol generating system further includes a liquid storage portion. In another embodiment, the liquid aerosol-forming substrate is stored in the liquid storage portion. In another embodiment, the heated aerosol generating system further includes a capillary wick in communication with the liquid storage portion. In another embodiment, it is also possible for a capillary wick for holding liquid to be provided without a liquid storage portion. In that embodiment, the capillary wick may be preloaded with liquid.

In another embodiment, the capillary wick is arranged to be in contact with liquid in the liquid storage portion. In that case, in use, liquid is transferred from the liquid storage portion towards the heater by capillary action in the capillary wick. In the preferred embodiment, the capillary wick has a first end and a second end, the first end extending into the liquid storage portion for contact with liquid therein and the at least one heater being arranged to heat liquid in the second end. When the heater is activated, the liquid at the second end of the capillary wick is vaporized by the heater to form the supersaturated vapor.

In another embodiment, the liquid has physical properties, including viscosity, which allow the liquid to be transported through the capillary wick by capillary action. In another embodiment, the liquid storage portion is a container. In another embodiment, the container is opaque, thereby limiting degradation of the liquid by light. In another embodiment, the liquid storage portion may not be refillable. Thus, when the liquid in the liquid storage portion has been used up, the smoking system is replaced. In another embodiment, the liquid storage portion may be refillable. In that case, the aerosol generating system may be replaced after a certain number of refills of the liquid storage portion. In another embodiment, the liquid storage portion is arranged to hold liquid for a pre-determined number of puffs.

In another embodiment, the capillary wick may have a fibrous or spongy structure. For example, the capillary wick may include a plurality of fibers or threads. The fibers or threads may be generally aligned in the longitudinal direction of the aerosol generating system. In another embodiment, the capillary wick may include sponge-like or foam-like material formed into a rod shape. The rod shape may extend along the longitudinal direction of the aerosol generating system. The structure of the wick forms a plurality of small bores or tubes, through which the liquid can be transported to the heater, by capillary action. The capillary wick may include any suitable material or combination of materials. Examples of suitable materials are ceramic- or graphite-based materials in the form of fibers or sintered powders. The capillary wick may have any suitable capillarity and porosity so as to be used with different liquid physical properties such as density, viscosity, surface tension and vapor pressure. The capillary properties of the wick, combined with the properties of the liquid, ensure that the wick is always wet in the heating area.

In another embodiment, the heated aerosol generating system may include at least one air inlet. The heated aerosol generating system may include at least one air outlet. The heated aerosol generating system may include an aerosol-forming chamber between the air inlet and air outlet. In use, when the heater is activated, the liquid in the capillary wick is vaporized by the heater to form a supersaturated vapor. The supersaturated vapor is mixed with and carried in the airflow from the at least one air inlet. During the flow, the vapor condenses to form an aerosol in the aerosol-forming chamber, and the aerosol is carried towards the air outlet into the mouth of a user.

The liquid has physical properties, for example a boiling point suitable for use in the smoking system: if the boiling point is too high, the at least one heater will not be able to vaporize liquid in the capillary wick, but, if the boiling point is too low, the liquid may vaporize even without the at least one heater being activated. The liquid preferably includes a tobacco-containing material including volatile tobacco flavor compounds, which are released from the liquid upon heating. Alternatively, or in addition, the liquid may include a non-tobacco material. The liquid may include water, solvents, ethanol, plant extracts and natural or artificial flavors. Preferably, the liquid further includes an aerosol former. Examples of suitable aerosol formers are glycerine and propylene glycol.

Alternatively, the aerosol-forming substrate may be a solid aerosol-forming substrate. The aerosol-forming substrate includes a tobacco-containing material containing volatile tobacco flavor compounds, which are released from the substrate upon heating. The aerosol-forming substrate may include a non-tobacco material. The aerosol-forming substrate may include tobacco-containing material and non-tobacco containing material. Preferably, the aerosol-forming substrate further includes an aerosol former. Examples of suitable aerosol formers are glycerine and propylene glycol.

The solid substrate may include, for example, one or more of: powder, granules, pellets, shreds, spaghettis, strips or sheets containing one or more of: herb leaf, tobacco leaf, fragments of tobacco ribs, reconstituted tobacco, extruded tobacco such as homogenized tobacco and expanded tobacco. The solid substrate may be in loose form, or may be provided in a suitable container or cartridge. Optionally, the solid substrate may contain additional tobacco or non-tobacco volatile flavor compounds, to be released upon heating of the substrate.

Optionally, the solid substrate may be provided on or embedded in a thermally stable carrier. In a preferred embodiment, the carrier is a tubular carrier having a thin layer of the solid substrate deposited on its inner surface, or on its outer surface, or on both its inner and outer surfaces. Such a tubular carrier may be formed of, for example, a paper, or paper like material, a non-woven carbon fiber mat, a low mass open mesh metallic screen, or a perforated metallic foil or any other thermally stable polymer matrix.

Alternatively, the carrier may take the form of powder, granules, pellets, shreds, spaghettis, strips or sheets. The solid substrate may be deposited on the surface of the carrier in the form of, for example, a sheet, foam, gel or slurry. The solid substrate may be deposited on the entire surface of the carrier, or alternatively, may be deposited in a pattern in order to provide a non-uniform flavor delivery during use. Alternatively, the carrier may be a non-woven fabric or fiber bundle into which tobacco components have been incorporated. The non-woven fabric or fiber bundle may include, for example, carbon fibers, natural cellulose fibers, or cellulose derivative fibers.

Further, an aerosol is a suspension of solid particles or liquid droplets in a gas, such as air. The aerosol may be a suspension of solid particles and liquid droplets in a gas, such as air.

In one embodiment, the invention provides for an electrically heated aerosol generating system for receiving an aerosol-forming substrate, the system including at least one electric heater for heating the aerosol-forming substrate to form the aerosol, the heater including a heating element electrically connected to an electrical source.

In one embodiment, the heating element is formed of a thermally and/or electrically conductive material.

In one embodiment, the heating element may be made from an elastic material. In another embodiment, the heating element may be made from a flexible material. In another embodiment, the heating element may be formed by shaping from a sheet of electrically resistive material. In another embodiment, the heating element may be pre-formed in the desired shape.

In another embodiment, the heater is an electric heater for an electrically heated smoking system having a capillary wick for holding liquid. In another embodiment, the at least one electric heater may include a single heating element. In another embodiment, the at least one heater may include more than one heating element, for example two, or three, or four, or five, or six or more heating elements. In that case, each heating element may extend between an electrically positive connector and an electrically negative connector. The heating element or heating elements may be arranged appropriately so as to most effectively heat the aerosol-forming substrate. In the embodiment in which a capillary wick is provided, the heating element or heating elements may be arranged appropriately so as to most effectively vaporize liquid in the capillary wick.

Suitable electrically resistive materials for the heating element include but are not limited to: semiconductors such as doped ceramics, electrically conductive ceramics (such as, for example, molybdenum disilicide), carbon, graphite, metals, metal alloys and composite materials made of a ceramic material and a metallic material. Such composite materials may include doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium-titanium-zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys.

In composite materials, the electrically resistive material may optionally be embedded in, encapsulated or coated with an insulating material or vice-versa, depending on the kinetics of energy transfer and the external physicochemical properties required. The heating element may include a metallic etched foil insulated between two layers of an inert material. In that case, the inert material may include Kapton®, all-polyimide or mica foil. The at least one heater may additionally include a disk (end) heater or a combination of a disk heater with heating needles or rods.

In another embodiment, all portions of the heating element may have the same cross sectional shape and area. Alternatively, some portions of the heating element may have a different cross sectional shape from other portions of the heating element.

In another embodiment, the aerosol generating system may further include an electric power supply. In one embodiment, the electric power supply includes a cell contained in a housing. In another embodiment, the electric power supply may be a lithium-ion battery or one of its variants, for example a lithium-ion polymer battery. In another embodiment, the power supply may be a nickel-metal hydride battery, a Nickel cadmium battery, a lithium-manganese battery, a lithium-cobalt battery or a fuel cell. In another embodiment, the heated smoking system is usable by a smoker until the energy in the power cell is used up.

In another embodiment, the electric power supply may include circuitry chargeable by an external charging portion. In that case, preferably the circuitry, when charged, provides power for a pre-determined number of puffs, after which the circuitry must be re-connected to the external charging portion. An example of suitable circuitry is one or more capacitors or rechargeable batteries.

In another embodiment, the smoking system may further include electric circuitry. In another embodiment, the electric circuitry includes a sensor to detect airflow indicative of a user taking a puff. The sensor may be an electro-mechanical device. In another embodiment, the sensor may be any of: a mechanical device, an optical device, an opto-mechanical device, a micro electro mechanical systems (MEMS) based sensor and an acoustic sensor. In that case, preferably, the electric circuitry is arranged to provide an electric current pulse to the at least one heater when the sensor senses a user taking a puff. In another embodiment, the time-period of the electric current pulse is pre-set, depending on the amount of liquid desired to be vaporized. In another embodiment, the electric circuitry is programmable for this purpose. In another embodiment, the electric circuitry may include a manually operable switch for a user to initiate a puff. In another embodiment, the time-period of the electric current pulse is pre-set depending on the amount of liquid desired to be vaporized.

In another embodiment, the heated aerosol generating system includes at least one air inlet. There may be one, two, three, four, five or more air inlets. Preferably, if there is more than one air inlet, the air inlets are spaced around the heated aerosol generating system. In another embodiment, the electric circuitry includes a sensor to detect airflow indicative of a user taking a puff, and the at least one air inlet is upstream of the sensor.

In another embodiment, the aerosol generating system further includes an indicator for indicating when the at least one heater is activated. In the embodiment in which the electric circuitry includes a sensor to detect airflow indicative of a user taking a puff, the indicator may be activated when the sensor senses airflow indicative of the user taking a puff. In the embodiment in which the electric circuitry includes a manually operable switch, the indicator may be activated by the switch.

The device may also include a detector. The detector may be a modular assembly comprising a sensor and an actuation circuit, which may be mounted on a printed circuit board. In one embodiment, the sensor can be an airflow sensor for detection of inhalation.

In another embodiment, the sensor can be a capacitance sensor for detection of contact of the device or part of the device with fingers, lips or other parts of the body. In one embodiment, the capacitance sensor for detection of contact can trigger a timer for auto shutdown.

As the conductive will need to respond rapidly to repeated inhaling and to return to its neutral or standby condition quickly or immediately after inhaling stops, a metallic sheet having a good axial resilience property is preferred to be used as the conductive membrane. The conductive back plate is connected to an earth plate (124), which is in turn mounted on a PCB, by a conductive ring (125) to form a reference ground of the capacitive component. This sub-assembly of the air-flow sensor and PCB is housed within a metallic can (126) which defines an air inlet and an air outlet at its axial ends.

In another embodiment, the heated aerosol generating system may further include an atomizer including the at least one heater. In addition to a heating element, the atomizer may include one or more electromechanical elements such as piezoelectric elements. Additionally or alternatively, the atomizer may also include elements that use electrostatic, electromagnetic or pneumatic effects.

In another embodiment, the aerosol generating system includes a housing. In another embodiment, the housing is elongate. If the aerosol generating includes a capillary wick, the longitudinal axis of the capillary wick and the longitudinal axis of the housing may be substantially parallel. The housing may include a shell and a mouthpiece. In that case, all the components may be contained in either the shell or the mouthpiece. In another embodiment, the electric power supply and the electric circuitry are contained in the shell. Preferably, the liquid storage portion, if included, the capillary wick, if included, the heater and the air outlet are contained in the mouthpiece. The at least one air inlet, if included, may be provided in either the shell or the mouthpiece. In the preferred embodiment, the housing includes a removable insert including the liquid storage portion, the capillary wick and the heater. In that embodiment, those parts of the aerosol generating system may be removable from the housing as a single component. This may be useful for refilling or replacing the liquid storage portion, for example.

In another embodiment, the mouthpiece is replaceable. Having a shell and a separate mouthpiece provides a number of advantages. Firstly, if the replaceable mouthpiece contains the heater, the liquid storage portion and the wick, all elements that are potentially in contact with the liquid are changed when the mouthpiece is replaced. There will be no cross-contamination in the shell between different mouthpieces, for example ones using different liquids. Also, if the mouthpiece is replaced at suitable intervals, there is little chance of the heater becoming clogged with liquid. Preferably, the shell and mouthpiece are arranged to releasably lock together when engaged.

In another embodiment, the housing may include any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

In another embodiment, the aerosol generating system is portable. In another embodiment, the aerosol generating system may be a smoking system and may have a size comparable to a conventional cigar or cigarette. In another embodiment, the smoking system may have a total length ranging from about 30 mm to about 100 mm. In another embodiment, the smoking system may have an external diameter ranging from about 5 mm to about 13 mm. When the heating element is folded around an aerosol-forming substrate, this may have a diameter ranging from about 3 mm to about 5 mm. In another embodiment, the heating element may have a cross section ranging from about 0.5 mm to about 1 mm. In another embodiment, the heating element may have a thickness ranging from about 0.1 mm to about 0.3 mm.

In another embodiment, the heating element heats up when electrical current is passed through it. The heater may be for a heated smoking system. The heater may be an electric heater for an electrically heated smoking system having a capillary wick for holding liquid. The heater may be arranged to heat liquid in at least a portion of the capillary wick to form the aerosol.

In yet another embodiment, there is also provided use of a heater according to the second aspect of the present invention as a heater to heat an aerosol-forming substrate in a catalytically heated aerosol generating system.

In another embodiment, the liquid material may be any commercially available liquid material suitable for use in commercial vaporized and/or aerosolized fragrance generators. The liquid material is preferably aqueous based, alcohol based, such as, for example, methanol, or propylene glycol based In another embodiment, the smoking system includes a capillary wick for holding liquid, at least one heater for heating the liquid in at least a portion of the capillary wick to form an aerosol, at least one air inlet, at least one air outlet and a chamber between the air inlet and air outlet, the air inlet, the air outlet and the chamber being arranged so as to define an air flow route from the air inlet to the air outlet via the capillary wick so as to convey the aerosol to the air outlet, and at least one guide for channeling the air flow in the air flow route, so as to control particle size in the aerosol.

In use, when the heater is activated, the liquid in the at least one portion of the capillary wick is vaporized by the heater to form a supersaturated vapor. The supersaturated vapor is mixed with and carried in the airflow from the at least one air inlet. During the flow, the vapor condenses to form an aerosol in the chamber, and the aerosol is carried towards the air outlet into the mouth of a user. As used herein, the upstream and downstream relative positions are described in relation to the direction of airflow as it is drawn from the air inlet to the air outlet.

The liquid has physical properties, for example a boiling point suitable for use in the smoking system: if the boiling point is too high, the at least one heater will not be able to vaporize liquid in the capillary wick, but, if the boiling point is too low, the liquid may vaporize even without the at least one heater being activated. In another embodiment, the liquid includes a tobacco-containing material including volatile tobacco flavor compounds, which are released from the liquid upon heating. Alternatively, or in addition, the liquid may include a non-tobacco material. For example, the liquid may include water, solvents, ethanol, plant extracts and natural or artificial flavors. Preferably, the liquid further includes an aerosol former. Examples of suitable aerosol formers are glycerine and propylene glycol.

In another embodiment, the smoking system further includes a liquid storage portion. Preferably, the capillary wick is arranged to be in contact with liquid in the liquid storage portion. In that case, in use, liquid is transferred from the liquid storage portion towards the heater by capillary action in the capillary wick. In one embodiment, the capillary wick has a first end and a second end, the first end extending into the liquid storage portion for contact with liquid therein and the at least one heater being arranged to heat liquid in the second end. When the heater is activated, the liquid at the second end of the capillary wick is vaporized by the heater to form the supersaturated vapor.

In another embodiment, the smoking system can further include a housing and the at least one guide for channeling the airflow is provided by the internal shape of the housing. That is to say, the internal shape of the assembly itself channels the airflow. In another embodiment, the inside surface of the housing walls have a shape which forms guides to channel the airflow. The guides provided by the internal shape of the housing may be provided upstream of the capillary wick. In that case, the guides channel the airflow from the air inlet towards the capillary wick. Alternatively or additionally, the guides provided by the internal shape of the housing may be provided downstream of the capillary wick. In that case, the guides channel the aerosol and airflow from the capillary wick towards the air outlet. In the preferred embodiment, the internal shape of the housing defines a tapered channel towards the air outlet.

In another embodiment, the internal shape of the housing may define a linear flow upstream or downstream of the capillary wick. Alternatively, the internal shape of the housing may define a swirled, that is to say, rotating or spiraling, flow upstream or downstream of the capillary wick. In yet another embodiment, the internal shape of the housing may define any turbulent flow upstream or downstream of the capillary wick.

Any material that is capable of being aerosolized and inhaled by a user may be incorporated into a device or cartridge of the invention as would be obvious to one skilled in the art. It is of particular interest that the material provides an experience to the user either in terms of tactile response in the respiratory tract, or in terms of visual feedback regarding the exhalation of the inhaled material. For example, many materials have be contemplated for use with the present invention including, but not limited to, those containing tobacco, natural or artificial flavorants, coffee grounds or coffee beans, mint, chamomile, lemon, honey, tea leaves, cocoa, and other non-tobacco alternatives based on other botanicals. A device or cartridge of the invention can also be compatible for use with pharmaceutical compounds or synthetic compounds, such as medicinal marijuana and THC, either for pharmaceutical or pleasurable use. Any such compound which can be vaporized (or volatized) at a relatively low temperature and without harmful degradation products can be suitable for use with a cartridge or device of the invention. Examples of compounds include, but are not limited to, menthol, caffeine, taurine, THC and nicotine.

Active elements contained in botanicals vaporize at different temperatures. The device can be calibrated to establish a single stable temperature, intended for vaporizing specific products, for example. A controller can also be used to select a variety of temperature settings. The user would choose which setting based on the type of cartridge used. The controller can also affect a desired temperature mechanically, such as by changing flow rate of the valve, or electronically, such as by electromechanical valve and micro-controller intermediary.

Here, tobacco or tobacco material is defined as any combination of natural and synthetic material that can be vaporized for pleasure or medicinal use. In one embodiment of the present invention, a cartridge can be prepared using cured tobacco, glycerin, and flavorings. Those skilled in the art of tobacco product manufacture are familiar with these and other ingredients used for cigarettes, cigars, and the like. The cartridge can be produced by chopping tobacco into fine pieces (for example, less than 2 mm diameter, preferably less than 1 mm), adding the other ingredients, and mixing until even consistency was achieved. In another embodiment, a cartridge can be prepared by processing the fill material into an even paste-like consistency (for example, particle size less than 1 mm), which facilitates the processing of filling the cartridge, for example, by use of an auger filler, peristaltic pump or a piston pump.

In one embodiment, the material for use with a device of the invention or contained within a cartridge of the invention comprises at least one of a vapor-forming medium and a medium for providing a tactile response in a respiratory tract of a user. In another embodiment, the aerosolized product from the material inserted into a device can be a combination of vapor phase gases as well as small droplets which have condensed out of vapor phase and remain suspended in the gas/air mixture (the latter constitutes the visible portion of the inhaled substance).

Propylene glycol (PG), glycerin, or a combination of both can be used as vapor-forming medium. Other vapor-forming media can be used with a cartridge and device of the invention. In another embodiment, the vapor-forming medium serves to produce a visual vapor, such as a smoke-like vapor, when heated. This vapor can be visualized both before inhalation and during exhalation of the medium. PG has some advantages as compared to glycerin alone, as it exhibits a much higher vapor pressure at equivalent temperature and allows the device to operate at a lower temperature. Reducing the operating temperature conserves energy, and potentially can further improve the health benefits of using this system.

In another embodiment, the vapor resulting from PG that is inhaled by the user can partially absorb in the respiratory tract. If this occurs, it can appear as though the user is expelling primarily air. This differs from the conventional smoking experience in that in the case of smoking, users can typically see and play with expelled smoke as they exhale. Because the visual vapor created by heating glycerin can be seen upon exhale, some preparation of fill material for this invention can comprise a combination of both glycerin and PG. In these embodiments, the PG allows for high densities of visual vapor which the user can see/experience prior to inhaling as well as a tactile response in the respiratory tract, and the addition of glycerin allows for increased amounts of vapor to be seen or otherwise experienced upon exhale.

In one embodiment, the invention provides for a catalyst having high oxygen reduction reactivity and low methanol oxidation reactivity. In one embodiment, the invention provides for a supported catalyst.

According to an aspect of the present invention, there is provided a supported catalyst, wherein the whole substrate or at least the surface of the substrate comprises one or more metals selected from the group consisting of Fe, Co, Ni, Rh, Pd, Pt, Cu, Ag, Au, Zn, and Cd. In one embodiment, the invention provides for a supported catalyst, wherein the whole substrate or at least the surface of the substrate comprises an alloy of two or more metals selected from the group consisting of Fe, Co, Ni, Rh, Pd, Pt, Cu, Ag, Au, Zn, and Cd.

In one embodiment, the invention provides for an alloy contained in the whole or at least the surface of a catalyst substrate may be a binary alloy selected from the group consisting of Cd and Au; Cd and Ag; Cd and Cu; Cd and Ni; Cd and Pd; Cd and Pt; Zn and Au; Zn and Ag; Zn and Cu; Zn and Ni; Zn and Pd; Zn and Pt; Cu and Pd; Cu and Pt; and Ag and Pt.

In one embodiment, the invention provides for catalyst substrates made of alloys of three or more metals selected from the group consisting of Fe, Co, Ni, Rh, Pd, Pt, Cu, Ag, Au, Zn, and Cd.

In one embodiment, the whole catalyst substrate may comprise an alloy of two or more metals selected from the group consisting of Fe, Co, Ni, Rh, Pd, Pt, Cu, Ag, Au, Zn, and Cd.

In another embodiment, at least the surface of the catalyst substrate may comprise an alloy of two or more metals selected from the group consisting of Fe, Co, Ni, Rh, Pd, Pt, Cu, Ag, Au, Zn, and Cd.

The oxygen binding force or the hydrogen binding force of the catalyst substrate is determined by the surface component of the catalyst substrate which binds with oxygen or hydrogen. That is, although the inner portion of the catalyst substrate has any compositions, when the surface of a catalyst substrate is coated with an alloy of two or more metals selected from the group consisting of Fe, Co, Ni, Rh, Pd, Pt, Cu, Ag, Au, Zn, and Cd, the objects of the present invention can be accomplished.

In one embodiment, the catalyst active components comprise precious metals and/or transition metals, which may be Pt, Pd, Rh, Ir, Ru, Ni, Os, Re, Co, Fe, Mn, Cu, Ag, Au, or combinations thereof. In one embodiment, the active catalyst component is Pt, which may be used alone or may be promoted by any main group metal, non-metal, transition metal compound or combinations thereof. In one embodiment, the active compound is used in the reduced state. In one embodiment, the catalyst activity and stability may be increased by the addition of a catalyst promoter. This can be transition metal such as nickel, cobalt, Al, Si, Ce, or Zr or mixtures thereof. Typical metal promotor content may be from 0%-10% by weight.

The catalyst of the present invention may be supported. The support can be any stable inert support, such as alumina, modified alumina, silica, a molecular sieve, such as zeolite Y, silicon carbide or any inert material composite. In order to increase the stability of the support, the support may be modified using other compounds.

In one embodiment, the metal oxide catalyst comprises one or more transition metal oxide comprising oxides of metal elements selected from a group of Sc, T, V, Cr, Mn, Fe, Ni, Cu, Zn, Y, Zr, Nb, Mo, Tc, Ru, Rh, Pd, Ag, Cd, La, Hf, Ta, W, Re, Os, Ir, Pt, Au, Ce, Pr, Nd, Pm, Sm, Eu, Gd, Tb, Dy, Ho, Er, Tm, Yb, Lu, and mixtures thereof, wherein transition metal oxide has mono, multiple oxidation states, or mixtures thereof. In another embodiment, the transition metal oxides herein comprising oxides of metal elements selected from a group of Fe, Co, Ni, Cu, Ru, Rh, and mixtures thereof). In another embodiment, the metal oxide catalyst comprises one or more transition metal oxides coupled with one or more non-transition metal oxides, wherein non-transition metal comprises Li, Na, Sr, K, Rb Cs, Fr, Mg, Ca, Sr, Ba, Ra, Al, Si, Fe, Ga, In, Sn, Pb or mixtures thereof. Some mixed-metal oxides show an inhibiting effect on hydrogen generation. Oxides of metal elements selected from Mo, Zn, V, W, and so on may be used for controlling reaction rates. By coupling with these metal elements with active metal oxides containing elements of Fe, Co, Cu, Ni, Ru, Rh and mixtures thereof, desirable reaction rate can be achieved for specific applications.

The metal oxide catalyst can have a form of powder, wire, chip, disk, rod, strip, bead, monolith with/without porosity, or metal oxide substrates supported on a substrate comprising metals, ceramics, polymers, glass, fibers, fabrics, textiles, wovens, nonwovens, fibers, alloys, zeolites, molecular sieves, ion exchange resins, graphite, metal oxide, metal carbide, metal boride, metal nitride, and mixtures thereof.

In all embodiments of the present invention, it is preferable that the catalyst used in the present invention is any solid catalyst that is able to catalyze the reaction of the reactants to produce the product mixture comprising steam. In another embodiment, the catalyst is a solid transition metal or noble metal catalyst that is able to catalyze the reaction of the reactants to produce the product mixture.

Another embodiment of the invention is to make metal oxide catalyst by thermal decomposition of metal compounds. Precursors of metal oxide catalysts may be, without limitation, metal fluoride, metal chloride, metal bromide, metal iodide, metal nitrate, metal carbonate, metal hydroxide, metal borate, metal acetate, metal oxalate, or an organometallic compound. For the preparation of metal oxide or mixed-metal oxide powder with high surface area, a glycine-nitrate method is employed. The size and porosity of the metal substrates can be controlled by adjusting the amount of glycine.

A supported metal oxide catalyst is prepared through a decomposition process of a metal compound that is bound to, entrapped within, and coated on a substrate comprising metals, ceramics, polymers, glass, fibers, fabrics, textiles, wovens, nonwovens, fibers, alloys, zeolites, molecular sieves, ion exchange resins, graphite, metal oxide, metal carbide, metal boride, metal nitride, and mixtures thereof. Coating of metal film on a substrate can be achieved by an electroplating or electrodeless plating process. Catalytic beds can be used comprised of platinum and other catalytic materials dispersed over ceramic fiber or rock wool bed.

In one embodiment, the fuel can be any organic compound that can supply energy through its oxidation. In one embodiment, the fuel is a short chain (e.g., C1-C6) alcohol, ketone, aldehyde, or carboxylic acid that is readily oxidized. In another embodiment, the fuel is an alcohol such as methanol, ethanol, propanol, or isopropanol. In another embodiment, the alcohol is ethanol or methanol.

It should be mentioned that this type of combustion can be used to safely combust a variety of fuels. Catalytically combustible gases such as, for example, hydrogen, carbon monoxide, methane, propane, pentane, ether, ethane, butane, ethanol, propanol, and other hydrocarbon compounds may also be used.

In one embodiment, the present invention may be used with a gaseous hydrocarbon such as butane, which is allowed to flow onto a catalytic substrate, such as a platinum mesh, and then combust. The fuel, for example hydrogen, methane, ethane, propane or butane, combines with oxygen and liberates heat, which then heats the platinum mesh. In this embodiment, the temperature of the mesh stabilizes at the combustion temperature of the fuel, for example butane, thereby allowing combustion to occur on the surface of the platinum mesh. In one embodiment, the air, which is heated, is isolated from the air which is used for combustion to generate heat and which contains combustive gases. To accomplish this, combustion occurs within a sealed system.

The hydrocarbon gas does not need to be stored in a gas state. For example, complex metal borohydrides M(BH4)n can be used for in situ production of hydrogen gas. Li or Na borohydrides are usually used as a source of BH4-group but borohydrides of other metals (K, Ca, Al, Be, Zn, Mg, Sc, and/or Ti,) can also be used.

Suitably, at least one metal of the electrochemical catalyst nanoparticles is selected from the group comprising one or more of Pt, Au, Pd, Ru, Re, Rh, Os, Ir, Fe, Co, Ni, Cu, Ag, V, Cr, Mo, W and alloys or mixtures thereof.

Turning to the Drawings, wherein like numerals indicate like components throughout the several views, in FIG. 1, a device 100 is provided for vaporizing a liquid for inhalation (E-Liquid) 102. A housing 104 has a proximal exit orifice 106 that communicates with an intake orifice 108. A reservoir 110 may be encompassed by the housing 104 and contains the liquid 102. A wick 112 has a first end 114 in contact with the liquid 102 and a second end 116 that is exposed at an opening 118 in the reservoir 110. A heater 120 may be disposed within the housing 104 in an air passage 122 that communicates between the intake orifice 108 and the proximal exit orifice 106. An actuator 124 responds to an input 126 by a user of the device 100 to place the heater 120 and the second end 116 of the wick 118 into proximity with the heater 120 to vaporize the liquid 102, to join air flow 128 through the air passage 122.

In FIGS. 2-3, a device 200 in one particular embodiment utilizes a catalytic heater 220. In addition, the device 200 causes atomization or vaporization of the liquid 102. In another aspect, the device 200 has a pneumatic actuator 224 linked for movement with a reservoir 210 containing the liquid 102. A housing 204 has a proximal exit orifice 206 that communicates with an intake orifice 208. The reservoir 210 may be encompassed by the housing 204 and contains the liquid 102. A wick 212 has a first end 214 in contact with the liquid 102 and a second end 216 that is exposed at an opening 218 in the reservoir 210. The catalytic heater 220 may be disposed within the housing 204 in an air passage 222 that communicates between the intake orifice 208 and the proximal exit orifice 206.

The catalytic heater 224 includes a distal combustion chamber 230 having a distal opening 232 disposed in the housing 204 for receiving an ignition source 234 (FIG. 2) and for air exchange as depicted at 235, 236 (FIG. 3). A vessel 238 may be encompassed within the housing 204 to dispense a catalytic fuel 240 to the combustion chamber 230. In the exemplary embodiment, a wick tube 242 communicates between the vessel 238 and the combustion chamber 230. Thereby, a fuel wick 244 in the wick tube 242 may transfer the catalytic fuel 240 to react with a catalyst 245 in the combustion chamber 230. A barrier 246 between the combustion chamber 230 and the air passage 222 is also breached by a thermally conductive surface 248 that is heated by the combustion chamber 230 and that extends distally into the air passage 222.

The pneumatic actuator 224 includes a plunger 250 received for longitudinal movement in a plunger chamber 252 formed in a portion of the air passage 222. The plunger 250 is connected via a linkage 254 to the reservoir 210. The pneumatic actuator 224 responds to an input 256 by a user of the device 200, which is a low pressure at the proximal exit orifice 206. As depicted in FIG. 2, compression spring 258 in the plunger chamber 252 biases the plunger 250 proximally toward the intake orifice 208, and correspondingly spaces apart the wick 212 from the thermally conductive surface 248. When the plunger 250 compresses the compression spring 258 as depicted in FIG. 3, thermally conductive surface 248 of the catalytic heater 220 is brought into proximity to the wick 212 sufficient to atomize or vaporize the liquid 102 as depicted at 260.

In FIGS. 4-5, a device 300 for atomizing or vaporizing a liquid for inhalation incorporates a pneumatic actuator 324 that moves the heater, which in this instance is a catalytic heater 320 in response to the user input 256 (drawing air from the exit orifice 306). To that end, a combustion chamber 330 is received for longitudinal movement into a housing 304 for movement by the pneumatic actuator 324.

The housing 304 has a proximal exit orifice 306 that communicates with an intake orifice 308. A reservoir 310 may be encompassed by the housing 304 and contains the liquid 102. A wick 312 has a first end 314 in contact with the liquid 102 and a second end 316 that is exposed at an opening 318 in the reservoir 310. The catalytic heater 320 may be disposed within the housing 304 in an air passage 322 that communicates between the intake orifice 308 and the proximal exit orifice 306.

The catalytic heater 324 includes the distal combustion chamber 330 having a distal opening 332 disposed in the housing 304 for receiving an ignition source 334 (FIG. 4) and for air exchange as depicted at 335, 336 (FIG. 5). A vessel 338 may be encompassed within the housing 304 to dispense the catalytic fuel 240 to the combustion chamber 330. In the exemplary embodiment, a wick tube 342 communicates between the vessel 338 and the combustion chamber 330. Thereby, a fuel wick 344 in the wick tube 342 may transfer the catalytic fuel 240 to react with a catalyst 345 in the combustion chamber 330. A barrier 346 between the combustion chamber 330 and the air passage 322 is also breached by a thermally conductive surface 348 that is heated by the combustion chamber 330 and that extends distally into the air passage 322.

The pneumatic actuator 324 includes a plunger 350 received for longitudinal movement in a plunger chamber 352 formed in a proximal end of the body 304 and in a proximal portion of the air passage 322. The plunger 350 is connected via a linkage 354 to the vessel 338 and thus indirectly to the combustion chamber 330. The pneumatic actuator 324 responds to an input 356 by a user of the device 300, which is a low pressure at the proximal exit orifice 306. As depicted in FIG. 4, compression spring 358 in the plunger chamber 352 biases the plunger 350 distally, and correspondingly spaces apart the thermally conductive surface 348 from the wick 312. When the plunger 350 compresses the compression spring 358 as depicted in FIG. 5, thermally conductive surface 348 of the catalytic heater 320 is brought into proximity to the wick 312 sufficient to atomize or vaporize the liquid 102 as depicted at 360.

Figure 6:
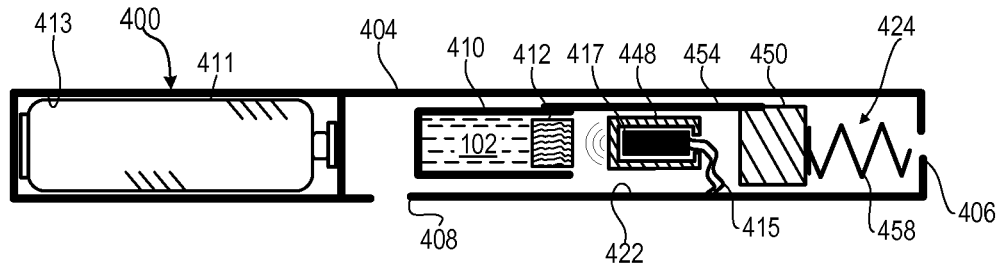
FIG. 6 depicts a diagram of a device for vaporizing a liquid for inhalation using an electric heater and another alternative pneumatic actuator, depicted in an unactuated state, according to one embodiment.
Figure 7:
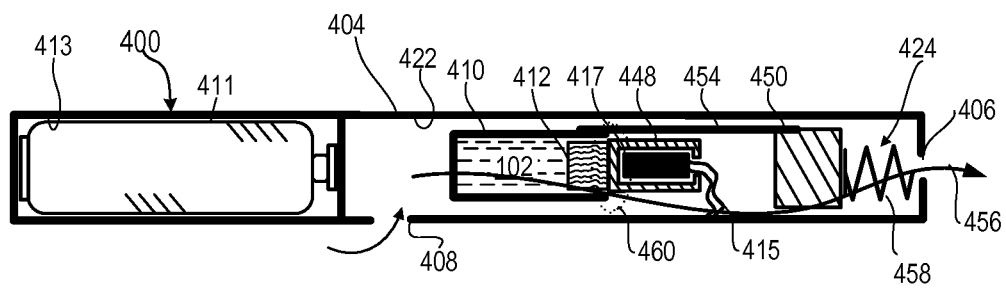
FIG. 7 depicts a diagram of the device of FIG. 6 in an actuated state.

In FIGS. 6-7, a device 400 for vaporizing a liquid for inhalation incorporates an electric heater 420 as well as utilizing a pneumatic actuator 424. A power supply, depicted as a battery 411 is isolated within a battery compartment 413 at a distal portion of a housing 404. The battery 411 is electrically connected via wires 415 to a thermal load 417 within a thermally conductive container 448. As depicted in FIG. 6, a compression spring 458 distally biases a plunger 450 positioned in a proximal portion of the housing 404. As a user inhales, drawing air from an exit orifice 406 in the housing 404 as depicted at 456, causing air to enter an intake orifice 408 and pass through air passage 422 to the exit orifice 406. The air pressure in the air passage 422 draws the plunger 450 proximally, compressing the compression spring 458, while moving aft a linkage a reservoir 410 containing the liquid 102 until a proximally facing wick 412 encounters the thermally conductive container 448, causing the liquid to vaporize as depicted at 460.

Figure 8:
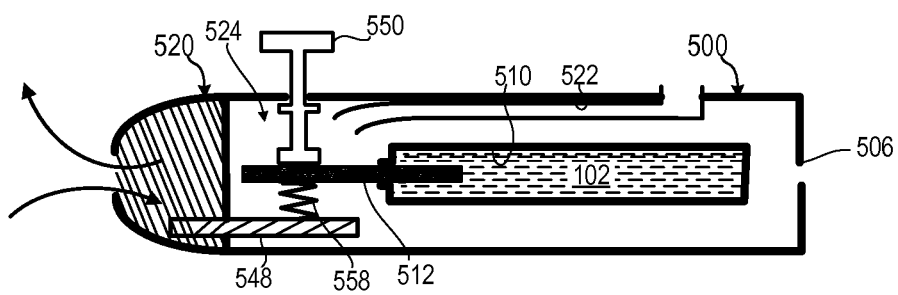
FIG. 8 depicts a diagram of a device for vaporizing a liquid for inhalation using a catalytic heater and a manual actuator, depicted in an unactuated state, according to one embodiment.
Figure 9:
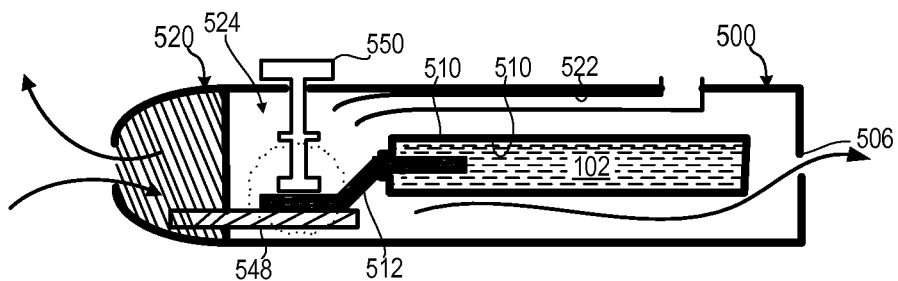
FIG. 9 depicts a diagram of the device of FIG. 10 in an actuated state.

In FIGS. 8-9, a device 500 includes a manual actuator 524 for moving a wick 512 into contact with a thermally conductive surface 548 of a catalytic heater 520. In FIG. 8, a compression spring 558 spaces apart the wick 512 from the thermally conductive surface 548. In FIG. 9, an external control 550 compresses the compression spring 558 to cause the wick 512 to come into contact with the thermally conductive surface 548 and thus vaporize the liquid 102. Then a user can draw from the proximal exit orifice 506 in the housing 504, drawing air into the intake orifice 508, through an air passage 522 in the device 502 to inhale the vaporized liquid 102.

Figure 10:
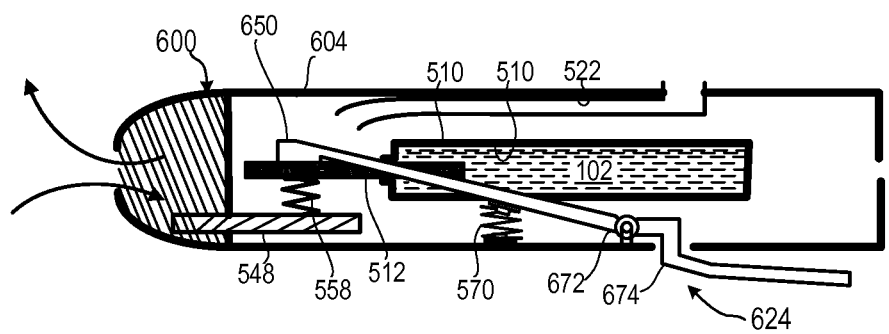
FIG. 10 depicts a diagram of a device for vaporizing a liquid for inhalation using a catalytic heater and mouth actuator, depicted in an unactuated state, according to one embodiment.
Figure 11:
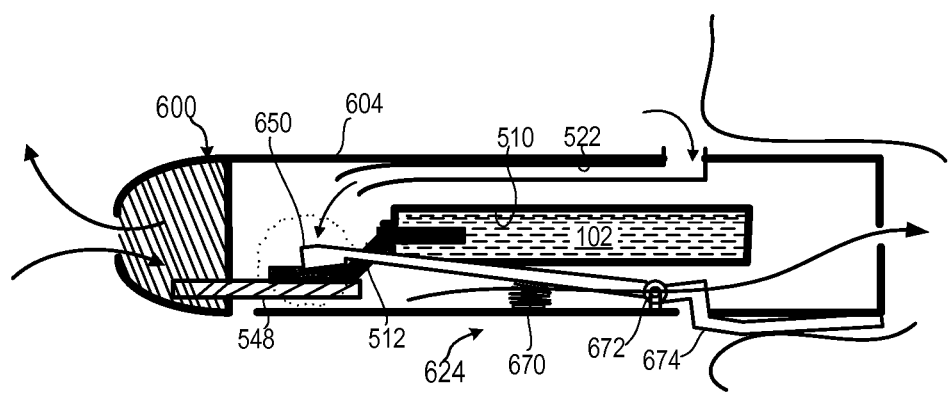
FIG. 11 depicts a diagram of the device of FIG. 10 in an actuated state.

In FIGS. 10-11, a device 600 that is otherwise similar to device 500 has a manual actuator 624 that is mouth actuated rather than finger actuated. In FIG. 10, the compression spring 558 raises the wick 512 and an opposing end of a lever 650. An additional biasing spring 670 pushes open the lever 650 distal to a pivoting mounting 672 to the housing 604. A proximal end 674 of the lever 650 is externally disposed for being moved by the user.

Figure 12:
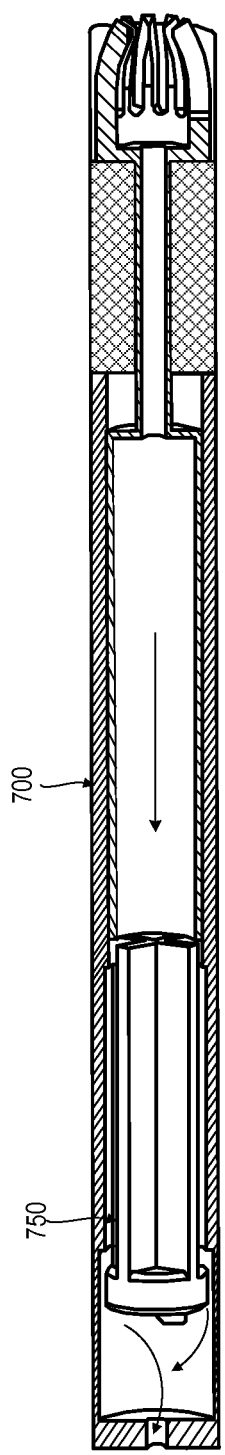
FIG. 12 depicts a side cross section view of a plunger for use in devices for vaporizing a liquid for inhalation.

In FIG. 12, an example of a mouth-actuated plunger 750 is depicted for use in device 700, which may be similar to other devices described herein is depicted. Then a user can draw from the proximal exit orifice in the housing, drawing air into the intake orifice (not shown), through an air passage in the device to inhale the vaporized liquid.

All publications, patents and patent applications cited herein, whether supra or infra, are hereby incorporated by reference in their entirety to the same extent as if each individual publication, patent or patent application was specifically and individually indicated as incorporated by reference. It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein, will only be incorporated to the extent that no conflict arises between that incorporated material and the existing disclosure material.

It must be noted that, as used in this specification and the appended claims, the singular forms "a," "an" and "the" include plural referents unless the content clearly dictates otherwise. Thus, for example, reference to a "colorant agent" includes two or more such agents.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

As will be appreciated by one having ordinary skill in the art, the methods and compositions of the invention substantially reduce or eliminate the disadvantages and drawbacks associated with prior art methods and compositions.

It should be noted that, when employed in the present disclosure, the terms "comprises," "comprising," and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

While it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments, which come within the spirit and scope of the present invention.

What is claimed is:

1. A device for vaporizing a liquid for inhalation, comprising:
   a housing having a proximal exit orifice that communicates with an intake orifice;
   a reservoir encompassed by the housing, and containing a liquid;
   a wick having a first end in contact with the liquid and a second end that is exposed at an opening in the reservoir;
   a heater disposed within the housing in an air passage that communicates between the intake orifice and the proximal exit orifice, the heater comprising a surface that extends in parallel to the second end of the wick; and
   an actuator responsive to a user of the device to place the heater and the second end of the wick into proximity with the heater to vaporize the liquid by deflecting the second end of wick into contact with the surface of the heater.

2. The device of claim 1, wherein the heater comprises an electrical heater.

3. The device of claim 2, wherein the heater comprises:
   a distal heating element in the housing for receiving an electrical current;
   a battery encompassed within the housing that dispenses an electrical current to the heating element; and
   a surface that is heated by the heating element;
   wherein the surface is a thermal conductor capable of storing heat energy and providing the heat energy to the liquid.

4. The device of claim 1, wherein the heater comprises a solid fuel heater.

5. The device of claim 4, wherein the heater comprises:
   a distal combustion chamber having a distal opening disposed in the housing for receiving an ignition source and for air exchange;
   a vessel encompassed within the housing that dispenses a solid fuel to the combustion chamber; and
   a surface that is heated by the combustion chamber;
   wherein the surface is a thermal conductor capable of storing heat energy and providing the heat energy to the liquid.

6. The device of claim 5, wherein the solid fuel comprises one or more of wood, charcoal, charcoal briquettes, lump charcoal, and mixtures thereof.

7. The device of claim 6, wherein the heater further comprises a retardant in the fuel to reduce the combustion rate.

8. The device of claim 1, wherein the heater comprises an exothermic reaction fuel heater.

9. The device of claim 8, wherein the heater comprises:
   a distal combustion chamber having a distal opening disposed in the housing for receiving an exothermic fuel and for air exchange;
   a vessel encompassed within the housing that dispenses an exothermic fuel to the combustion chamber; and
   a surface that is heated by the combustion chamber;
   wherein the surface is a thermal conductor capable of storing heat energy and providing the heat energy to the liquid.

10. The device of claim 9, wherein the exothermic fuel comprises one or more supercorroding metallic alloy powders.

11. The device of claim 10, wherein the supercorroding alloy powders are constructed from a metal selected from the group consisting of magnesium, iron, nickel and mixtures thereof.

12. The device of claim 1, wherein the heater comprises a catalytic heater.

13. The device of claim 12, wherein the heater comprises:
   a distal combustion chamber having a distal opening disposed in the housing for receiving an ignition source and for air exchange;
   a vessel encompassed within the housing that is capable of storing and dispensing a hydrogen-bearing fuel to the combustion chamber; and
   the surface that is heated by the combustion chamber;
   wherein the surface is a thermal conductor capable of storing heat energy and providing the heat energy to the liquid.

14. The device of claim 13, wherein the combustion chamber comprises a catalytic metal or alloy or composite.

15. The device of claim 14, wherein the catalytic metal is one or more metals selected from the group consisting of Fe, Co, Ni, Rh, Pd, Pt, Cu, Ag, Au, Zn, and Cd.

16. The device of claim 14, wherein the catalytic metal comprises an alloy of two or more metals selected from the group consisting of Fe, Co, Ni, Rh, Pd, Pt, Cu, Ag, Au, Zn, and Cd.

17. The device of claim 1, wherein the actuator places the wick into contact with the surface to vaporize the liquid.

18. The device of claim 1, wherein the actuator comprises a spring-biased pneumatic actuator that responds to suction at the proximal exit orifice.

19. The device of claim 1, wherein the actuator comprises a control disposed on an exterior of the housing that is positionable by user.

20. The device of claim 19, wherein the control is distally positioned for finger actuation.

21. The device of claim 19, wherein the control is proximally positioned for mouth actuation.

* * * * *